United States Patent
Sugawara et al.

[11] Patent Number: 5,808,729
[45] Date of Patent: Sep. 15, 1998

[54] FIBER-OPTIC BLOCK AND FINGERPRINT DETECTOR USING THE SAME

[75] Inventors: Takeo Sugawara; Toshihiko Hino; Kazuaki Okumura, all of Hamamatsu, Japan

[73] Assignee: Hamamatsu Photonics K.K., Shizuoka-ken, Japan

[21] Appl. No.: 872,674

[22] Filed: Jun. 11, 1997

[30] Foreign Application Priority Data

Jun. 11, 1996 [JP] Japan ..................................... 8-149402

[51] Int. Cl.⁶ ................................. G06K 9/74; G02B 6/04
[52] U.S. Cl. ........................... 356/71; 385/120; 385/121; 385/901
[58] Field of Search ...................... 356/71; 382/124–127; 385/155, 116, 120, 121, 117–119, 901

[56] References Cited

U.S. PATENT DOCUMENTS

| | | | |
|---|---|---|---|
| 3,906,520 | 9/1975 | Phillips | 354/62 |
| 4,932,776 | 6/1990 | Dowling, Jr. et al. | 356/71 |
| 5,426,296 | 6/1995 | Shikai et al. | 250/227.2 |
| 5,684,905 | 11/1997 | Sugawara et al. | 385/120 |
| 5,684,906 | 11/1997 | Sugawara | 385/120 |

FOREIGN PATENT DOCUMENTS 07174947   7/1995   European Pat. Off. .

*Primary Examiner*—David C. Nelms
*Assistant Examiner*—Amanda Merlino
*Attorney, Agent, or Firm*—Cushman Darby Cushman IP Group of Pillsbury Madison & Sutro, LLP

[57] ABSTRACT

A tapered FOB (20) obtained by forming optical absorbers on the outer surfaces of fibers and bundling these fibers is joined to a slant FOB (10) obtained by bundling fibers, and a CCD (60) is arranged at the output end face of the tapered FOB (20). The slant angle ($\beta_0$) of a detection surface (11) of the slant FOB (10) on which a fingertip is to be placed is set to an angle at which background light incident from air on the slant FOB (10) is not reflected as total internal reflection at the interface between the core and cladding of the slant FOB (10). The slant angle ($\beta_1$) of the tapered FOB (20) is set such that background light reaching the tapered FOB (20) becomes incident at the interface between the core and the cladding at an angle smaller than the critical angle at which total internal reflection occurs. Unwanted background light and illumination light are eliminated, and the S/N ratio of a fingerprint image to be detected can be increased.

22 Claims, 7 Drawing Sheets

FIBER-OPTIC BLOCK AND FINGERPRINT DETECTOR USING THE SAME

BACKGROUND OF THE INVENTION

1. Field of the Invention

The present invention relates to a fiber-optic block constituted by series-connecting fiber-optic blocks each obtained by bundling and integrating a plurality of optical fibers, and a fingerprint detector using the fiber-optic block.

2. Related Background Art

A fiber-optic block (FOB) obtained by bundling and integrating a plurality of optical fibers is used in the detection section of a fingerprint detector or the like. As such a fingerprint detector, a technique disclosed in U.S. Pat. No. 4,932,776 is known, and its arrangement is shown in FIGS. 8A and 8B. In this detector, illumination light beams from light sources 82, 84, 86, and 88 are incident on a detection surface 74 from the shoulder portion of a slant tapered FOB 70. When a finger touches the detection surface 74, differences in reflection of the illumination light beams on the detection surface 74 occur in accordance with the contact/non-contact pattern of the ridges/recesses on the skin surface of a fingertip with the detection surface 74. The reflected light beams from the detection surface 74 are transmitted and reduced through the tapered FOB 70 and emerge from an end face 80. The exit light beams are detected by a CCD 78 mounted on the end face 80, thereby obtaining an image corresponding to a fingerprint image.

The fingerprint image obtained by this system has a low S/N ratio due to the following reason. Of all the illumination light beams entering the FOB 70 from the four directions, only some light beams directly contribute to fingerprint detection, and the remaining light beams leak outside from the detection surface 74 and a side surface 75 of the tapered FOB 70. The amount of light reaching the end face 80 is small, and the resultant image becomes dark. As a result, the fingerprint image obtained by the detection surface 74 is adversely affected by the above factors, thus resulting in an image having a low S/N ratio.

The cause for the decrease in the S/N ratio will be described in detail with reference to FIG. 9. Reference symbols a, b, c, and d denote the paths of light rays coming from the illustrated directions. In this example, a core 71 has a refractive index of 1.62, a cladding 72 has a refractive index of 1.48, and a slant angle α is 30° to 40°.

The illumination light beams projected from the light sources 82, 84, 86, and 88 are incident on the FOB 80 and then propagate in the FOB 70 toward the detection surface 74. In this case, the light beams travel in the FOB 70 while repeating refraction and reflection. For this reason, light beams are incident on an arbitrary point O on the detection surface 74 from various directions. That is, as indicated by a to c, light beams which are nearly diffused light beams are incident on the arbitrary point O on the detection surface 74.

Of all the incoming illumination light beams on the point O on the detection surface 74, only light beams incident upward in the angular range of $\theta_1$ to $\theta_2$ with respect to a direction (OM line) perpendicular to the detection surface 74 are reflected by the detection surface 74. The reflected light beams propagate in the optical fibers while repeating total internal reflection and are output as signal light (lines a–a' and b–b') from the end face 80. The minimum incident angle of a ray subjected to total internal reflection at the interface between the core 71 and the cladding 72 is $\theta_3$.

Of all the light beams incident upward on the point O on the detection surface 74, an illumination light beam incident at an incident angle (within the angle aOM) smaller than $\theta_1$ directly emerges outside without being reflected on the detection surface 74. A light beam (e.g., the ray c) incident upward at an incident angle (exceeding the angle bOM) larger than $\theta_2$ with respect to OM is reflected by the detection surface 74, propagates while repeating refraction without total internal reflection at the interface between the core 71 and the cladding 72, and finally emerges from the end face 80. Alternatively, this light beam emerges outside from the side surface 75 of the FOB 70. Of all the light beams incident within the angle MON, a light beam incident at an incident angle larger than the critical angle $\theta_2$ with respect to the line OM is reflected by the detection surface 74, repeats refraction between the core 71 and the cladding 72, and emerges outside from the side surface 75. On the other hand, a light beam incident at an incident angle smaller than the critical angle $\theta_2$ directly emerges outside from the detection surface 74.

As an example, the values of $\theta_1$, $\theta_2$, and $\theta_3$ in FIG. 9 for slant angle α=40° are obtained as follows.

$1.62 \cdot \sin \theta_3 = 1.48 \cdot \sin 90° \rightarrow \theta_3 = 66.0°$ $1.62 \cdot \sin \theta_1 = 1 \cdot \sin 90° \rightarrow \theta_1 = 38.1°$ $\theta_2 = 90° - \{\alpha - (90° - \theta_3)\} \rightarrow \theta_2 = 74.0°$ In detecting a fingerprint, the fingertip is pressed on the detection surface 74. The skin surface of the fingertip has ridges and recesses which serve as a three-dimensional pattern. On the detection surface 74 portion corresponding to each recess of the three-dimensional pattern, the state remains the same as that before the fingertip is pressed. The reflected light beam of a light beam incident on this detection surface portion in the range of angles $\theta_1$ to $\theta_2$ is totally reflected in the optical fiber and transmitted to the end face 80. On the other hand, each ridge of the skin surface comes into tight contact with the detection surface 74, and an illumination light beam reaching the detection surface 74 portion corresponding to the ridge of the skin surface is absorbed or scattered and does not return to the optical fiber. For this reason, of all the illumination light beams illuminating the detection surface 74, the light beams reflected by the ridges of the skin surface cannot be detected, and a density pattern is detected as a fingerprint image at the end face 80.

The fingerprint image is thus detected at the end face 80. As described above, the light beam reaching the end face 80 as signal light is only some of the illumination light beams incident from the range between the rays a and b. Some of the light beams incident from a range except the range between the rays a and b and reflected by the detection surface 74 propagate while repeating refraction at the interface between the core 71 and the cladding 72, resulting in noise at the end face 80. As a consequence, a signal detected as the fingerprint image by an image pickup element such as a CCD 60 has a low S/N ratio.

The background light incident from the detection surface 74 will also be considered on the basis of FIG. 10. Reference symbols e, f, g, and h denote rays incident from the illustrated directions. Lines e–e', f–f' indicate the ray propagation paths.

The ray e along the detection surface 74 travels toward the end face 80 (line e–e') while it is totally reflected at the interface between the core 71 and the cladding 72 of the optical fiber. The ray f becomes incident on the optical fiber and then the core 71 at a minimum total internal reflection incident angle (critical angle $\theta_c$) and propagates while it is reflected as total internal reflection at the interface between the core 71 and the cladding 72. The ray g has a smaller incident angle on the FOB 70 than the ray f and is not totally reflected in the optical fiber. The ray g propagates toward the end face 80 while repeating refraction between the core 71 and the cladding 72. The ray h has the same behavior as that of the ray g, but travels toward the side surface 75.

The background light beams incident as noise are classified into light beams incident on the point O in the eOf and fOh ranges. The background light beam incident on the point O in the eOf range travels toward the end face 80 while it is reflected as total internal reflection in the optical fiber. The background light beam incident on the point O in the fOh range travels toward the end face 80 and the side surface 75 while repeating refraction at the interface between the core 71 and the cladding 72.

Of these two types of background light beams, all the light beams reaching the end face 80 become noise which lowers the S/N ratio of the signal to be detected.

The present invention has been made to solve the conventional problems described above, and has as its object to provide a fiber-optic block capable of obtaining a higher S/N ratio by removing noise caused by illumination light and noise caused by background light and a fingerprint detector using such fiber-optic block.

SUMMARY OF THE INVENTION

According to an aspect of the present invention, there is provided a fingerprint detector for detecting a fingerprint image of a fingertip pressed on a detection surface, comprising of a first and second fiber-optic blocks and CCD. The first fiber-optic block is constituted by bundling optical fibers each having a core and a cladding. It has a flat detection surface which is inclined by a predetermined angle $\beta_0$ with respect to an optical axis thereat and on which the fingertip is to be placed, a flat output end face opposing the flat detection surface and perpendicular to an optical axis thereat, and a flat incident surface which makes the angle $\beta_0$ with the detection surface and on which light for illuminating the fingertip is incident. The inclination angle $\beta_0$ being set to be smaller than a critical angle at which light coming from air on the core is reflected as total internal reflection at an interface between the core and the cladding of the first fiber-optic block. The second fiber-optic block is constituted by bundling a plurality of optical fibers each having a core and a cladding and covered by optical absorbers. It has an input end face inclined by a predetermined angle $\beta_1$ with respect to an optical axis thereat and joined to the first fiber-optic block and a flat output end face perpendicular to an optical axis thereat. The predetermined angle $\beta_1$ being set to be smaller than a critical angle at which background light coming from air through the first fiber-optic block is reflected as total internal reflection at an interface between the core and the cladding of the second fiber-optic block. And the CCD is arranged at the output end face of the second fiber-optic block and having photoelectric conversion pixels arranged two-dimensionally.

According to this fingerprint detector, light incident from air to the first fiber-optic block through the detection surface is not reflected as total internal reflection at the interface between the core and cladding of the first fiber-optic block. This light is not transmitted through one optical fiber. Light transmitted upon refraction between the core and the cladding is not reflected as total internal reflection between the core and cladding of the second fiber-optic block upon incidence on the second fiber-optic block. This light is not transmitted through one optical fiber, but enters the optical absorber formed on the corresponding cladding and is absorbed therein. This light attenuates and disappears in the second fiber-optic block, and does not reach the CCD. Therefore, a fingerprint image can be measured at a high S/N ratio.

Alternatively, the fingerprint detector according to the present invention may comprise a first, second and third fiber-optic blocks and CCD. The first fiber-optic block is constituted by bundling optical fibers each having a core and a cladding. It has a flat detection surface which is inclined by a predetermined angle $\beta_0$ with respect to an optical axis thereat and on which the fingertip is to be placed, a flat output end face opposing the flat detection surface and perpendicular to an optical axis thereat, and a flat incident surface which makes the angle $\beta_0$ with the detection surface and on which light for illuminating the fingertip is incident. The inclination angle $\beta_0$ being set to be smaller than a critical angle at which light coming from air on the core is reflected as total internal reflection at an interface between the core and the cladding of the first fiber-optic block. The second fiber-optic block is constituted by bundling a plurality of optical fibers each having a core and a cladding and covered by optical absorbers. It has an input end face inclined by a predetermined angle $\beta_1$ with respect to an optical axis thereat and joined to the first fiber-optic block and a flat output end face perpendicular to an optical axis thereat. The predetermined angle $\beta_1$ being set to be smaller than a critical angle at which background light coming from air through the first fiber-optic block is reflected as total internal reflection at an interface between the core and the cladding of the second fiber-optic block. The third fiber-optic block has an input end face joined to the output end face of the second fiber-optic block to allow light incident from the second fiber-optic block to propagate and emerge from an output end face of the third fiber-optic block. And the CCD is arranged at the output end face of the third fiber-optic block and has photoelectric conversion pixels arranged two-dimensionally.

As in the above aspect of the present invention, the background light is not transmitted by the first and second fiber-optic blocks, but attenuates upon refraction and absorption. The background light does not reach the third fiber-optic block. Therefore, measurement can be performed at a high S/N ratio.

In either arrangement, the inclination angle $\beta_0$ of the first fiber-optic block preferably satisfies $\beta_0 < \sin^{-1}(n_1/n_0) - \sin^{-1}(n/n_0)$ where n, $n_1$, and $n_2$ are the refractive indices of air, the core, and the cladding, respectively.

Under this condition, the background light coming from air is incident on the interface between the core and cladding of the first fiber-optic block at an angle smaller than the critical angle at which total internal reflection occurs. Therefore, the background light is free from total internal reflection and propagates while repeating refraction at the interface between the core and the cladding.

The predetermined angle $\beta_1$ of the second fiber-optic block preferably satisfies $\beta_1 < \sin^{-1}\{1/n_2(n_1^2-((n_0^2-n^2)^{1/2}\sin\beta_0+n_1\cos\beta_0)^2)^{1/2}\}+\sin^{-1}(n_3/n_2)$ where $n_2$ and $n_3$ are the refractive indices of the core and cladding of the optical fiber of the second fiber-optic block.

Under this condition, the background light incident on the second fiber-optic block is not reflected as total internal reflection at the interface between the core and cladding of the second fiber-optic block, but propagates toward the corresponding optical absorber through the corresponding cladding.

In either arrangement, the fiber-optic block directly coupled to the CCD may have a tapered shape for gradually reducing a sectional area of the fiber-optic block perpendicular to the optical axis from the input end face to the output end face.

With this arrangement, a reduced fingerprint image can be obtained, and a more compact detection element can be used.

Alternatively, the second fiber-optic block may have an input-side effective numerical aperture equal to or smaller than an output-side effective numerical aperture of the first fiber-optic block. With this arrangement, of all the light beams incident from a surface opposing the detection surface to illuminate the fingertip, the light beam directly transmitted through the first fiber-optic block is not transmitted through the second fiber-optic block. Therefore, measurement can be performed at a high S/N ratio.

In addition, the fingerprint detector may further comprise means for comparing an electrical fingerprint image output from the CCD with another fingerprint image. A person in question can be authenticated on the basis of this fingerprint image.

Further, the present invention also incorporates a fiber optics block constituting the above fingerprint detector. According to this fiber optics block, the background light is not transmitted through optical fibers constituting a fiber-optic block, but attenuates upon refraction and absorption. Therefore, measurement can be performed at a high S/N ratio.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

The preferred embodiments of the present invention will be described with reference to the accompanying drawings.

Figure 1:
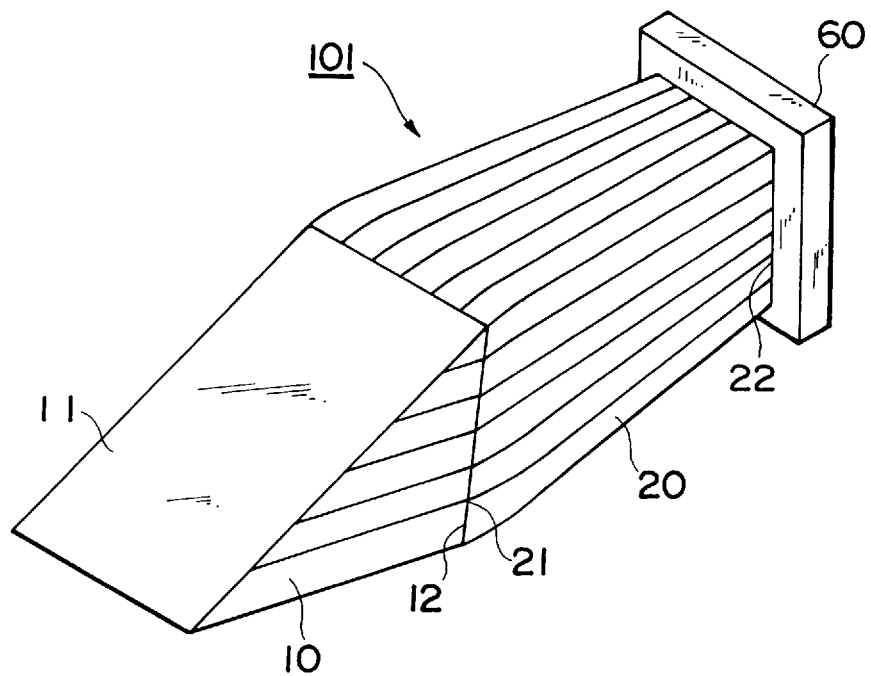
FIG. 1 is a perspective view showing a fingerprint detector according to an embodiment.
Figure 2:
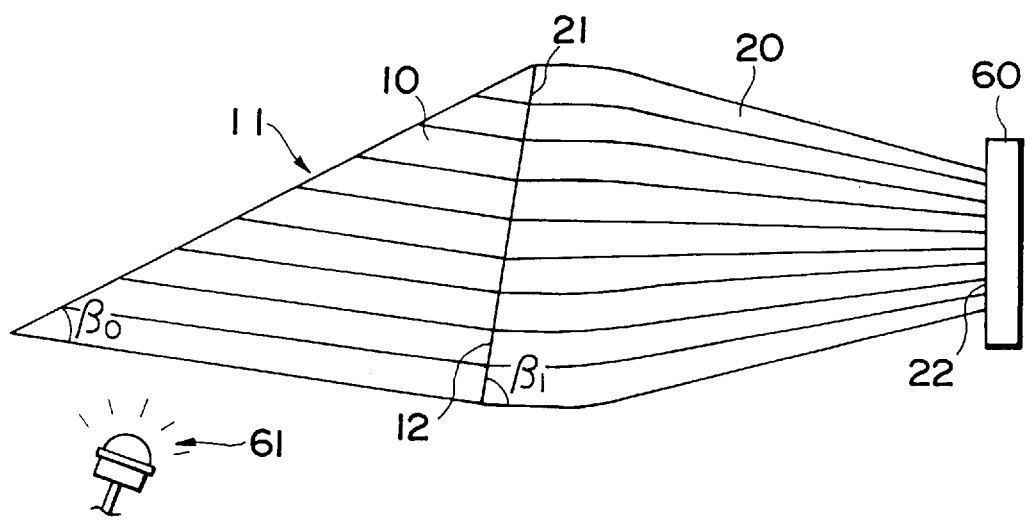
FIG. 2 is a side view of the fingerprint detector shown in FIG. 1.

FIG. 1 is a perspective view showing the outer appearance of a fingerprint detector 101 according to the present invention, and FIG. 2 is a schematic side view thereof. This fingerprint detector 101 has a fiber optics block obtained by joining a wedge-shaped slant FOB 10 and a tapered FOB 20 whose sectional area is gradually reduced from the light incident surface to the light exit surface. A CCD 60 is fixed to an output end face 22 of the tapered FOB 20. An illumination light source 61 is arranged underneath a detection surface 11 of the slant FOB 10 to illuminate the detection surface 11 from below. Note that the direction of optical fibers in each FOB is indicated by the solid lines on the side surface of each FOB.

Figure 3:
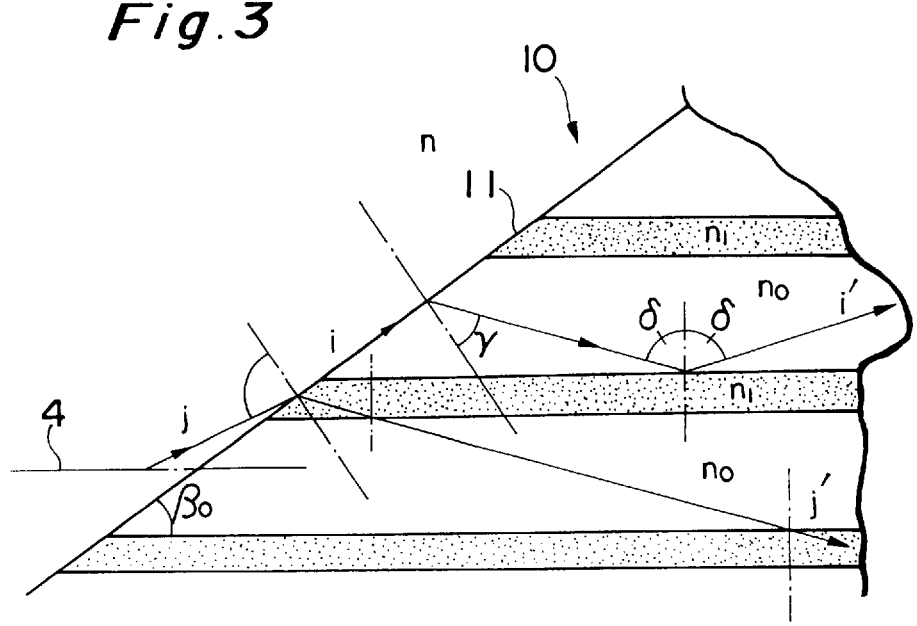
FIGS. 3 and 4 are enlarged longitudinal sectional views showing a portion near the detection surface of a slant FOB.

The slant FOB 10 is obtained by bundling and integrating a large number of optical fibers each consisting of a core 1 and a cladding 2 (see FIG. 3). The detection surface 11 serving as a fingertip press portion is cut at an angle (slant angle) $\beta_0$ with respect to an optical axis 4 (see FIG. 3) of the optical fiber (corresponding to the central axis of the optical fiber) at this surface. An output end face 12 is cut in a direction perpendicular to the optical axis of the optical fiber at this surface. Note that the inclination angle $\beta_0$ of the detection surface 11 will be described later.

Figure 5:
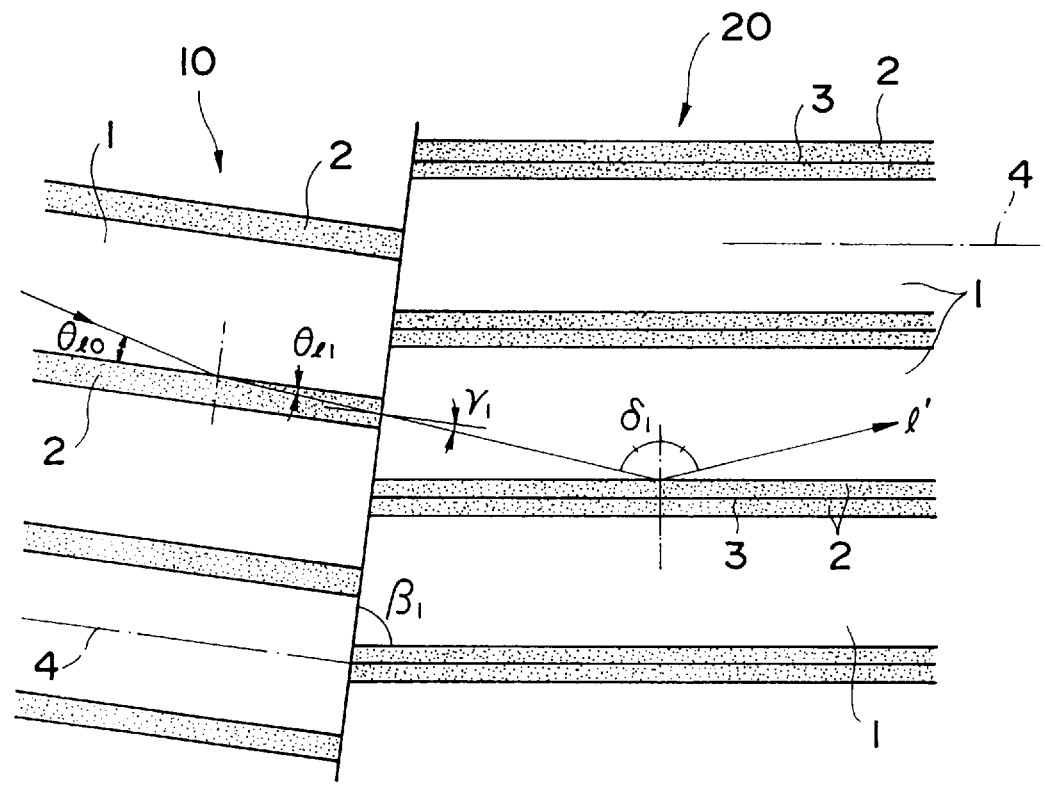
FIG. 5 is an enlarged longitudinal sectional view showing the joint portion between the slant FOB and a tapered FOB.

The tapered FOB 20 is similarly obtained by bundling and integrating a large number of fibers each consisting of a core 1 and a cladding 2 (see FIG. 5). In addition, optical absorbers 3 (see FIG. 5) are formed to cover the cladding 2 of the respective optical fibers. Each optical absorber consists of glass containing an oxide coloring agent of $Ni_2O_3$, $Co_2O_3$, $Cr_2O_3$, $CuO$, $Fe_2O_3$, or the like. The optical absorber has a function of absorbing light incident thereon to eliminate the light. An input end face 21 of the tapered FOB 20 which is joined to the output end face 12 of the slant FOB 10 is cut at an angle (slant angle) $\beta_1$ with respect to the optical axis of the optical fiber constituting the tapered FOB 20. The inclination angle $\beta_1$ of the input end face 21 will also be described later.

The function of the fingerprint detector 101 will be generally described below. In this fingerprint detector 101, a fingertip having ridges and recesses serving as a detection target is pressed on the detection surface 11. In this state, illumination light is irradiated on the detection surface 11 from the light source 61. Then, contact portions which contact the fingertip and non-contact portions are formed on the detection surface 11 in correspondence with the ridges and recesses of the skin surface of the fingertip. The contact portions are illuminated bright with the illumination light, while the non-contact portions are illuminated dark with the illumination light, thereby forming a density pattern. This pattern image propagates and is transmitted through the optical fibers of each FOB. The fingerprint pattern image is reduced upon transmission through the tapered FOB 20 and becomes incident on the CCD 60. The pattern image of the fingertip pressed on the detection surface 11 is detected as an electrical signal through the CCD 60.

This electrical signal is compared with another fingerprint image in a computer or the like described in U.S. Pat. No. 4,932,776. Upon collation, a person in question can be authenticated on the basis of a registered fingerprint image.

In the fingerprint detector 101 exemplified in this embodiment, the slant angle $\beta_0$ of the detection surface 11 of the slant FOB 10 and the slant angle $\beta_1$ of the input end face 21 of the tapered FOB 20 are set to predetermined angles so as to perfectly eliminate unwanted background light and the like from the detection surface 11 during propagation. This function will be described in detail below.

The background light beams incident from the detection surface 11 of the slant FOB 10 are two types of light beams: (I) a light beam transmitted through each optical fiber constituting the slant FOB 10; and (II) a light beam propagating while repeating refraction between a plurality of optical fibers like refraction of core-cladding-core . . . or refraction of cladding-core-cladding . . . . When these two types of background light beams enter the tapered FOB 20 within the light reception angle range of the tapered FOB 20, these light beams propagate through the optical fibers of the tapered FOB 20 and emerge from the output end face 22. As a result, the unwanted background light beams become noise for a fingerprint pattern image to be detected, thereby lowering the S/N ratio.

To remove the light beam (I) as noise, the slant angle $\beta_0$ is set as follows. FIG. 3 shows the optical path of light incident on the detection surface 11 of the slant FOB 10.

As shown in FIG. 3, background light incident on the core 1 portion of the detection surface 11 is refracted due to the difference in refractive index between air and the core and reaches the interface between the core 1 and the cladding 1 except when the optical path is parallel to the optical axis of the optical fiber. At this time, when the incident angle is a predetermined angle or more, the light is reflected as total internal reflection at the interface. Therefore, this background light propagates without being attenuated while repeating the above action. Light i incident parallel to the detection surface 11 is refracted and becomes light incident on the interface at a maximum incident angle. When the slant angle $\beta_0$ is so set not to totally reflect this light, the background light does not propagate through the slant FOB 10, thereby removing the background light noise.

When the refractive indices of air, the core material, and the cladding material of the slant FOB 10 are defined as n, $n_0$, and $n_1$, respectively, and the critical angle of total internal reflection and the maximum background light incident angle to the slant FOB 10 at the detection surface 11 are defined as $\delta$ and $\gamma$, respectively, the critical condition can be expressed as follows. First of all, the total internal reflection condition at the interface between the core 1 and the cladding 2 is written as:

$$\sin \delta = n_1/n_0 \quad (1)$$

From the condition that light i incident on the core 1 is refracted, $$n_0 \sin \gamma = n \sin 90° = n \quad (2)$$

From the geometric conditions of the respective angles, $$\beta_0 + (90°+\gamma) + (90°-\delta) = 180°$$

$$\beta_0 = \delta - \gamma \quad (3)$$

Rearranging equations (1) to (3) yields:

$$\beta_0 = \sin^{-1}(n_1/n_0) - \sin^{-1}(n/n_0) \quad (4)$$

When a slant angle $\beta_0$ smaller than determined by equation (4) is set, incident light i is not reflected as total internal reflection at the interface between the core 1 and the cladding 2. Light incident on the detection surface at an angle smaller than the light i enters the interface at an angle smaller than the critical angle $\delta$ upon refraction and is, of course, not reflected as total internal reflection. That is, light incident from air on the slant FOB 10 through the detection surface 11, i.e., the background light does not propagate in the direction of optical fibers in the FOB, but propagates while repeating refraction. Therefore, the light beam (I) is not generated, and noise caused by this light beam can be eliminated.

Figure 4:
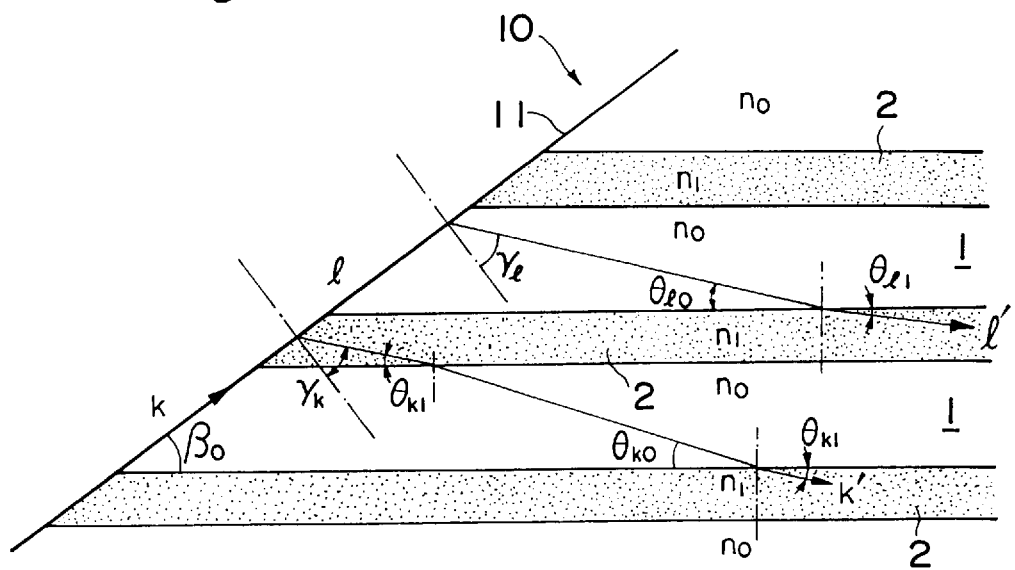

Removal of noise caused by the light beam (II) will be described below. The background light of this type propagates while repeating refraction in the optical fiber as in the ray j in FIG. 3. To remove this background light, the reception angle of the tapered FOB 20 is set to be smaller than the minimum incident angle of background light incident on the tapered FOB 20. FIG. 4 is a view showing the optical path of the light beam (II) in the slant FOB 10. FIG. 5 is a view showing the optical path of the light beam (II) at the joint surface between the slant FOB 10 and the tapered FOB 20.

The slant angle $\beta_0$ of the slant FOB 10 is set to a small value in consideration of the working precision in accordance with the critical angle $\beta_0$ obtained in equation (4). As shown in FIG. 4, of all the background light beams incident from the detection surface 11, beams incident on the tapered FOB 20 at small incident angles are rays k and l incident along the slant. Loci obtained upon incidence of the rays k and l on the cladding 2 and the core 1 are represented by lines k–k' and l–l', respectively. Incident angles $\gamma_k$ and $\gamma_l$ of the rays k and l on the detection surface and angles $\theta_{k0}$ and $\theta_{l0}$ and $\theta_{k1}$ and $\theta_{l1}$ of the optical paths with respect to the optical fibers at the core 1 and cladding 2 portions are expressed in accordance with the law of refraction as:

$$\sin \gamma_k = n/n_1 \quad (5)$$

$$\sin \gamma_l = n/n_0 \quad (6)$$

$$\theta_{k1} = 90° - (\beta_0 + \gamma_k) \quad (7)$$

$$\theta_{l1} = 90° - (\beta_0 + \gamma_l) \quad (8)$$

$$n_0 \sin(90° - \theta_{k0}) = n_1 \sin(90° - \theta_{k1}) \quad (9)$$

$$n_0 \sin(90° - \theta_{l0}) = n_1 \sin(90° - \theta_{l1}) \quad (10)$$

For the smallest incident angle, i.e., $\theta_{l1}$ with respect to the optical axis of the optical fiber in accordance with equations (5) to (10), a ray incident from the core 1 of the detection surface 11 and emerging from the cladding 2 of the output end face 12 is a ray having the smallest incident angle for the tapered FOB 20. Therefore, when the background light emerging from the slant FOB 10 at this minimum exit angle can be eliminated in the tapered FOB 20, all the background light beams incident on the tapered FOB 20 can be eliminated.

The ray propagation path shown in FIG. 5 is of a ray l of the background light incident from the core 1 of the detection surface 11 of the slant FOB 10 and emerging from the output end face 12. This ray is a ray emerging toward the tapered FOB 20 at the above-mentioned minimum incident angle $\theta_{l1}$. If the refraction angle upon incidence of the ray on the tapered FOB 20 is represented by $\gamma_1$, the following equation holds in accordance with the rule of refraction:

$$n_1 \sin \theta_{l1} = n_2 \sin \gamma_1 \quad (11)$$

where $n_2$ is the refractive index of the core 1 of the tapered FOB 20. If the refractive index of the cladding 2 is represented by $n_3$, a critical angle $\delta_1$ obtained upon total internal reflection of this ray at the interface between the core 1 and the cladding 2 is given by:

$$\sin \delta_1 = n_3/n_2 \quad (12)$$

$$\beta_1 + (90° - \gamma_1) + (90° - \delta_1) = 180°$$

$$\beta_1 = \gamma_1 + \delta_1 \quad (13)$$

where $\beta_1$ is the angle the joint surface of the tapered FOB 20 makes with the optical axis of the optical fiber.

Rearranging equations (6), (8), (10), and (11) to (13) gives:

$$\beta_1 = \sin^{-1}\{1/n_2(n_1^2-((n_0^2-n^2)^{1/2}\sin\beta_0+n_1\cos\beta_0)^2)^{1/2}\}+\sin^{-1}(n^3/n^2) \quad (14)$$

If $\beta_1$ is smaller than the value calculated by equation (14), the ray l' is not reflected as total internal reflection at the interface between the core 1 and cladding 2 of the tapered FOB 20, but is refracted to be directly incident on the cladding 2. All the background light beams represented by the light beam (II) are incident on the tapered FOB 20 at angles smaller than that of the ray l'. For this reason, these background light beams are not reflected as total internal reflection at the interface between the core 1 and the cladding 2 but refracted toward and incident on the cladding 2. Such a ray incident on the cladding 2 travels while repeating refraction between the cladding 2 and the core 1 and is absorbed by the corresponding optical absorber 3 during refraction. Therefore, the ray gradually attenuates during propagation and finally disappears. The light beam (II) is attenuated in this fashion.

If the refractive index of the cores 1 of the slant FOB 10 and the tapered FOB 20 is 1.560, and the refractive index of the cladding 2 thereof is 1.520, the critical angle of the slant angle $\beta_0$ of the slant FOB 10 is 37.13° from equation (4). However, this critical angle is preferably set to be $\beta_0 = 36°$ slightly smaller than the theoretical critical angle in consideration of the actual working precision. At this time, the critical angle of the slant angle $\beta_1$ of the tapered FOB 20 is calculated to be 82.44° from equation (13). In this case, the slant angle $\beta_1$ is preferably set to 82° in consideration of the actual working precision.

Figure 6:
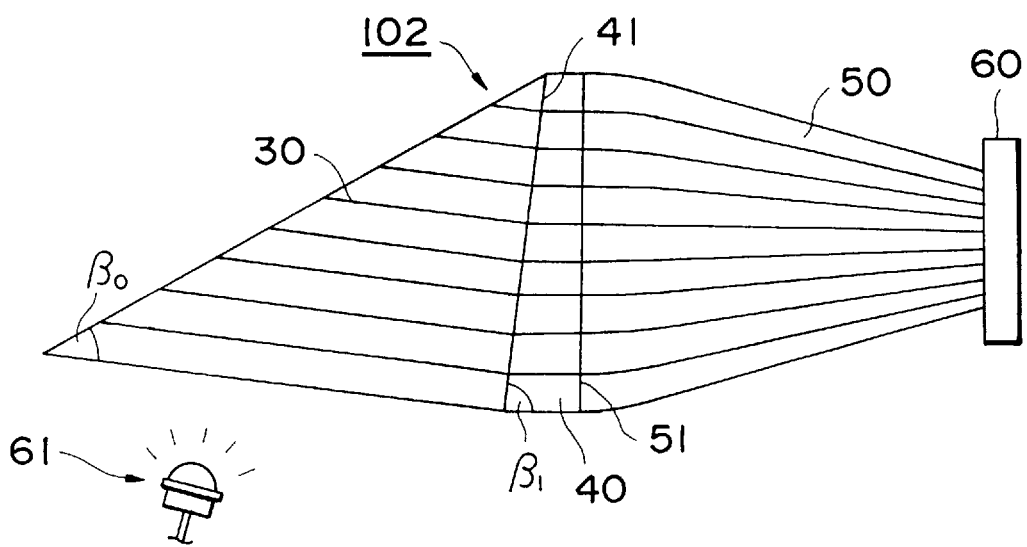
FIG. 6 is a perspective view showing a fingerprint detector according to another embodiment.

Another embodiment of the present invention is shown in FIG. 6. The fiber-optic block of a fingerprint detector 102 is constituted by joining a slant FOB 40 with optical absorbers between a slant FOB 30 without optical absorbers and a tapered FOB 50. With this structure, an FOB having the same function as the FOB 101 can be arranged. In this case, the slant FOB 30 corresponds to the slant FOB 10 previously described. The slant angle of the FOB 30 similarly conforms to the above-mentioned slant angle $\beta_0$. An input end face 51 of the tapered FOB 50 is cut in a direction almost perpendicular to an optical axis 4 of an optical fiber constituting this tapered FOB 50. The slant angle of an input end face 41 of the slant FOB 40 connected to the input side of the tapered FOB 50 is set to the slant angle $\beta_1$ of the above-mentioned slant FOB 20.

In the fingerprint detector 102 having the above arrangement, background light incident from the slant FOB 30 can be eliminated by the slant FOB 40 having the optical absorbers. The effective N.A. (Numerical Aperture) of the tapered FOB 50 can be freely selected as compared with the above embodiment.

In the fiber optics block of each fingerprint detector 101 (102), noise caused by the illumination light from the light source 61 can be removed if the N.A. of the FOB 20 (40) coupled to the output side of the slant FOB 10 (30) is equal to or smaller than that of the corresponding slant FOB 10 (30) and is a slant FOB having the optical absorbers 3. The reason for this will be described below.

Figure 7:
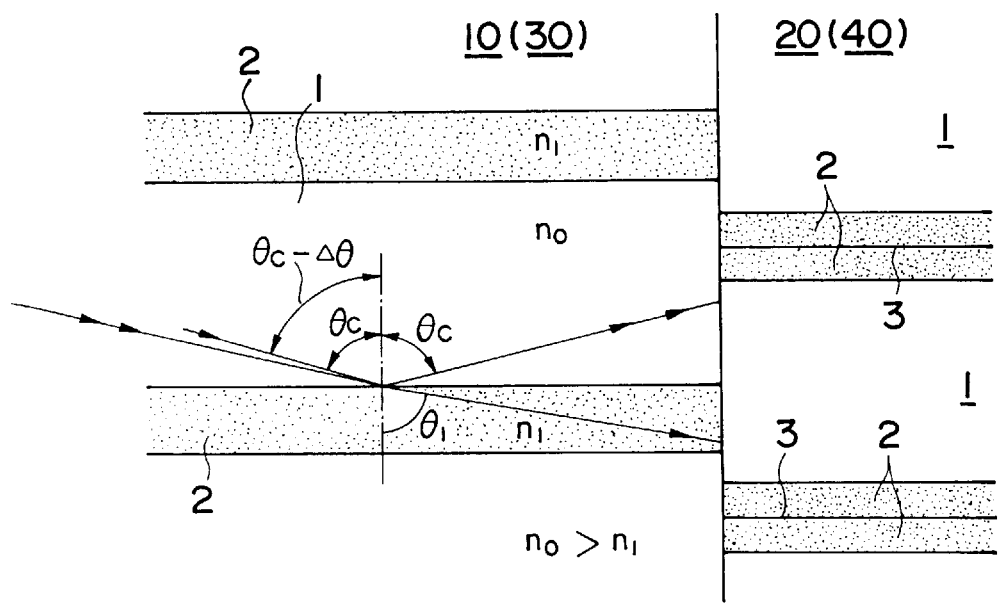
FIG. 7 is an enlarged longitudinal sectional view of an FOB joint portion.

FIG. 7 is an enlarged illustrated view of the joint surface between the adjacent FOBs 10 (30) and 20 (40). An output-side effective numerical aperture N.A.eff$_1$ of the slant FOB 10 (30) can be expressed as:

$$N.A.\text{eff}_1 = (n_0^2 - n_1^2)0.5 \quad (15)$$
$$= n_0 \sin(90° - \theta_c)$$
$$= n_0 \cos\theta_c$$

where $\theta_c$ is the critical angle at which total internal reflection occurs. On the other hand, a maximum effective numerical aperture N.A.eff$_2$ of the subsequent FOB 20 (40) must satisfy the following equation in order not to allow background light to propagate and to eliminate noise:

$$N.A.\text{eff}_2 = n_1 \sin(90° - \theta_1) \quad (16)$$
$$= n_0 \cos\theta_1$$

Since the above effective numerical apertures are positive values, squaring them and calculating the difference between the squares yields:

$$(N.A.\text{eff}_1)^2 - (N.A.\text{eff}_2)^2 = n_2 \cdot \cos^2\theta_c - n_1^2 \cdot \cos^2\theta_1$$
$$= n_0^2 \cdot \cos^2\theta_c - n_1^2 \cdot (1 - \sin^2\theta_1)$$
$$= n_0^2 \cdot \cos^2\theta_c - n_1^2 + n_1^2 \cdot \sin^2\theta_1$$
$$= n_0^2 \cdot \cos^2\theta_c - n_1^2 + n_0^2 \cdot \sin^2(\theta_c - \Delta\theta)$$
$$= n_0^2 \{\cos^2\theta_c + \sin^2(\theta_c - \Delta\theta)\} - n_1^2$$

(where $\theta_c - \Delta\theta$ is the incident angle of the background light).
If $\Delta\theta \to 0$, then the above equation can be rewritten as $$(N.A.\text{eff}_1)^2 - (N.A.\text{eff}_2)^2 \approx n_0^2 - n_1^2$$

therefore, the N.A.eff$_1$ value is found to be larger than the N.A.eff$_2$ value. It follows from the above result that the effective numerical aperture capable of eliminating the background light beam (II) is smaller than the output-side effective numerical aperture of the slant FOB 10 (30), and noise caused by the illumination light from the light source can also be removed.

This holds when the slant angle $\beta_1$ of the tapered FOB 20 or the slant FOB 40 is 90°. As described above, to eliminate the background light beam (II), however, the slant angle must be smaller than 90°. When the slant angle is smaller than 90°, the effect of removing the noise caused by the illumination light from the light source 61 can be further enhanced.

Figure 8A:
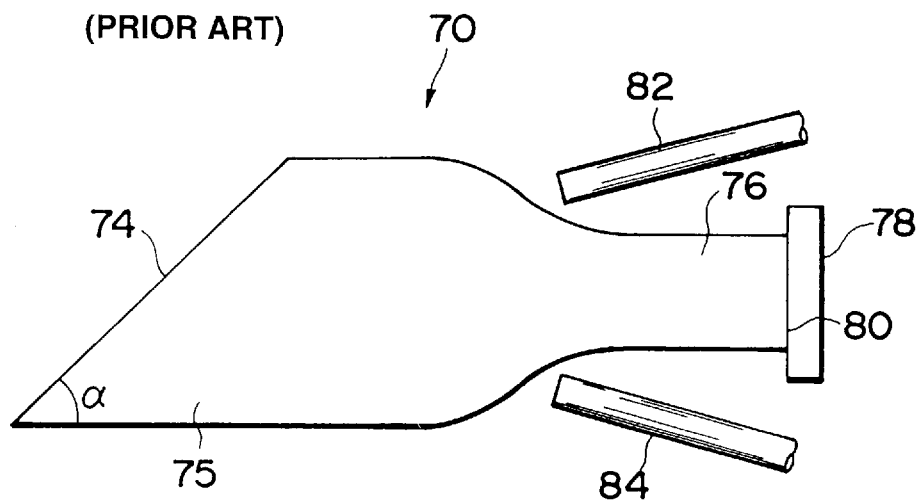
FIG. 8A is a side view showing a conventional fingerprint detector.
Figure 8B:
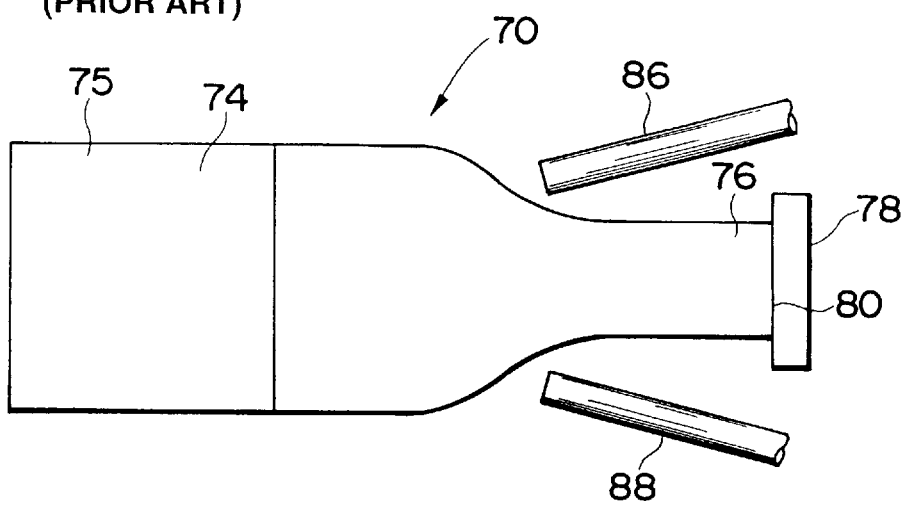
FIG. 8B is a top view of the fingerprint detector shown in FIG. 8A.
Figure 9:
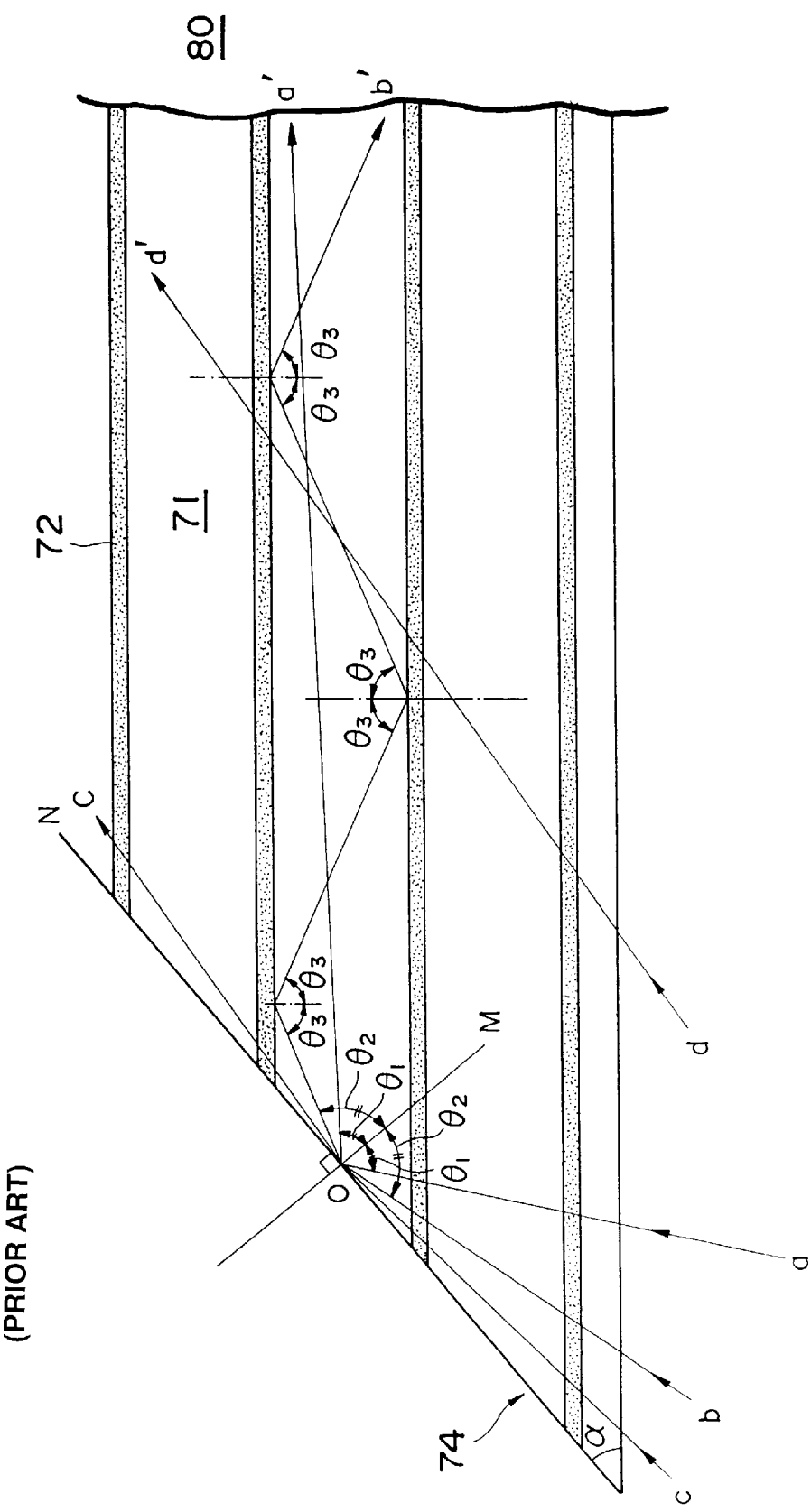
FIGS. 9 and 10 are enlarged longitudinal sectional views of a portion near the detection surface of the fingerprint detector shown in FIGS. 8A and 8B.
Figure 10:
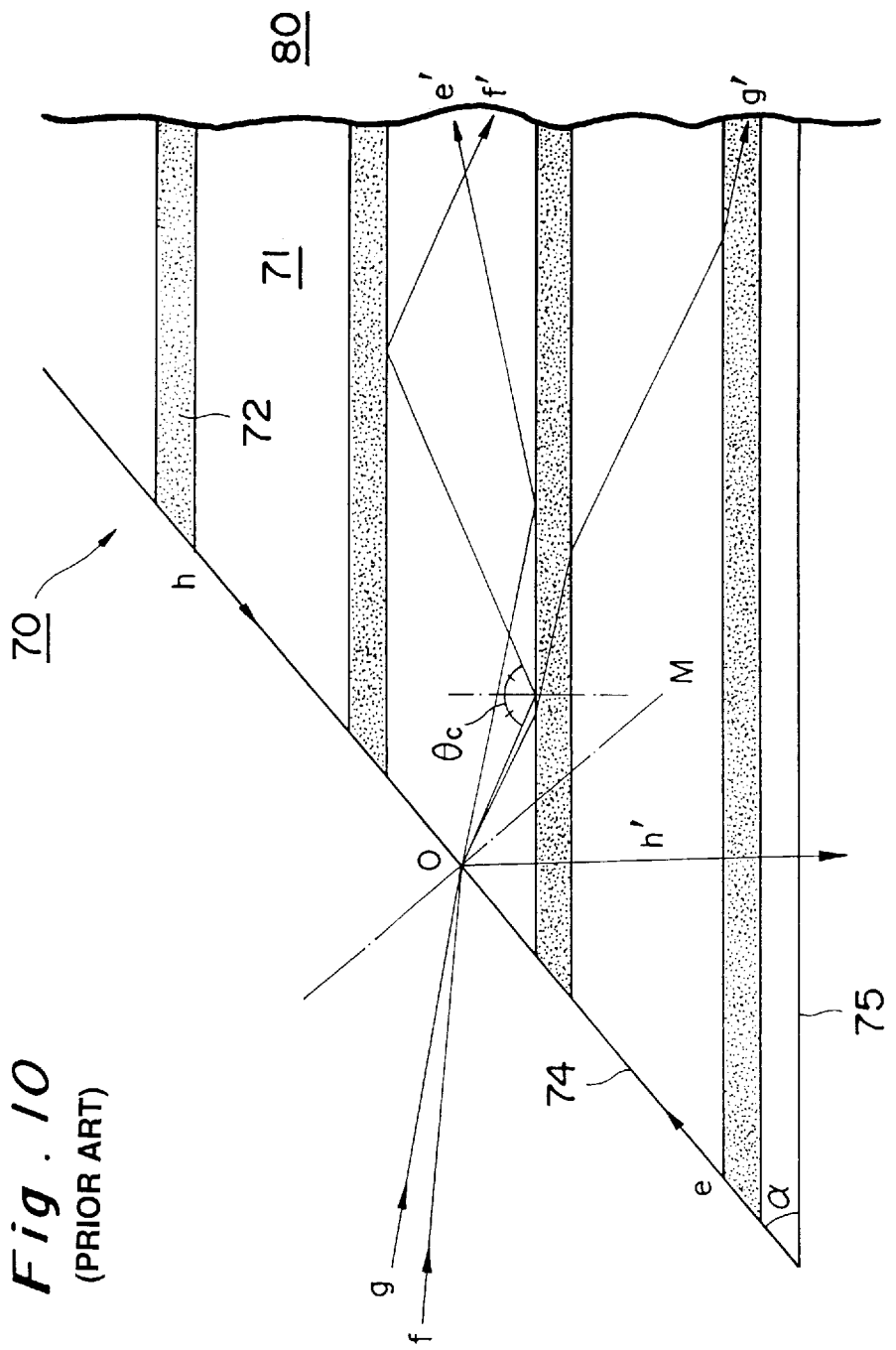

In either embodiement, the illumination light is only upward incident on the detection surface. As compared with conventional apparatus as shown in FIG. 8, the downward light incident on the detection surface is not occur, the S/N ratio of fingerprint pattern is improved.

As described above, according to the fiber optics block of the present invention, unwanted background light and illumination light which are detected as noise can be removed. Therefore, this can greatly improve the S/N characteristics of images detected by these fiber optics blocks.

In addition, since the subsequent fiber-optic block is made to have a tapered shape, a fingerprint image or the like an be transmitted and output as a reduced image, thereby allowing a more compact image pickup element or the like to detect the transmitted image.

In the fingerprint detector according to the present invention, a compact image pickup element can detect a fingerprint image having a high S/N ratio.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 149402/1996 filed on Jun. 11, 1996 is hereby incorporated by reference.

What is claimed is:

1. A fingerprint detector for detecting a fingerprint image of a fingertip pressed on a detection surface, comprising:

a first fiber-optic block which is constituted by bundling optical fibers each having a core and a cladding and has a flat detection surface which is inclined by a predetermined angle $\beta_0$ with respect to an optical axis thereat and on which the fingertip is to be placed, a flat output end face opposing said flat detection surface and perpendicular to an optical axis, and a flat incident surface which adjoins said detection surface making the angle $\beta_0$ therewith and on which light for illuminating the fingertip is incident, the inclination angle $\beta_0$ being set to be smaller than a critical angle at which light coming from air on said core is reflected as total internal reflection at an interface between said core and said cladding of said first fiber-optic block;

a second fiber-optic block which is constituted by bundling a plurality of optical fibers each having a core and a cladding and covered by optical absorbers and has an input end face inclined by a predetermined angle $\beta_1$ with respect to an optical axis thereat and joined to said first fiber-optic block and a flat output end face perpendicular to an optical axis thereat, the predetermined angle $\beta_1$ being set to be smaller than a critical angle at which background light coming from air through said first fiber-optic block is reflected as total internal reflection at an interface between said core and said cladding of said second fiber-optic block; and a CCD arranged at said output end face of said second fiber-optic block and having photoelectric conversion pixels arranged two-dimensionally.

2. A detector according to claim 1, wherein the inclination angle $\beta_0$ of said first fiber-optic block satisfies $\beta_0 < \sin^{-1} (n_1/n_0) - \sin^{-1} (n/n_0)$ where n, $n_1$, and $n_2$ are the refractive indices of air, said core, and said cladding of said first fiber-optic block, respectively.

3. A detector according to claim 1, wherein the predetermined angle $\beta_1$ of said second fiber-optic block satisfies $\beta_1 < \sin^{-1} \{1/n_2(n_1^2 - ((n_0^2 - n^2)^{1/2} \sin \beta_0 + n_1 \cos \beta_0)^2)^{1/2}\} + \sin^{-1} (n_3/n_2)$ wherein $n_2$ and $n_3$ are the refractive indices of said core and cladding of said second fiber-optic block.

4. A detector according to claim 1, wherein said second fiber-optic block has a tapered shape for gradually reducing a sectional area of said second fiber-optic block perpendicular to the optical axis from said input end face to said output end face.

5. A detector according to claim 1, wherein said second fiber-optic block has an input-side effective numerical aperture which is not more than an output-side effective numerical aperture of said first fiber-optic block.

6. A detector according to claim 1, further comprising means for comparing an electrical fingerprint image output from said CCD with another fingerprint image.

7. A fingerprint detector for detecting a fingerprint image of a fingertip pressed on a detection surface, comprising:

a first fiber-optic block which is constituted by bundling optical fibers each having a core and a cladding and has a flat detection surface which is inclined by a predetermined angle $\beta_0$ with respect to an optical axis thereat on which the fingertip is to be placed, a flat output end face opposing said flat detection surface and perpendicular to an optical axis thereat, and a flat incident surface which makes the angle $\beta_0$ with said detection surface and on which light for illuminating the fingertip is incident, the inclination angle $\beta_0$ being set to be smaller than a critical angle at which light coming from air on said core is reflected as total internal reflection at an interface between said core and said cladding of said first fiber-optic block;

a second fiber-optic block which is constituted by bundling a plurality of optical fibers each having a core and covered by optical absorbers and has an input end face inclined by a predetermined angle $\beta_1$ with respect to an optical axis thereat and joined to said first fiber-optic block and a flat output end face perpendicular to an optical axis thereat, the predetermined angle $\beta_1$ being set to be smaller than a critical angle at which background light coming from air through said first fiber-optic block is reflected as total internal reflection at an interface between said core and said cladding of said second fiber-optic block;

a third fiber-optic block having an input end face joined to said output end face of said second fiber-optic block to allow light incident from said second fiber-optic block to propagate and emerge from an output end face of said third fiber-optic block; and a CCD arranged at said output end face of said third fiber-optic block and having photoelectric conversion pixels arranged two-dimensionally.

8. A detector according to claim 7, wherein the inclination angle $\beta_0$ of said first fiber-optic block satisfies $\beta_0 < \sin^{-1} (n_1/n_0) - \sin^{-1} (n/n_0)$ where n, $n_1$, and $n_2$ are the refractive indices of air, said core, and said cladding of said first fiber-optic block, respectively.

9. A detector according to claim 7, wherein the predetermined angle $\beta_1$ of said second fiber-optic block satisfies $\beta_1 < \sin^{-1} \{1/n_2(n_1^2 - ((n_0^2 - n^2)^{1/2} \sin \beta_0 + n_1 \cos \beta_0)^2)^{1/2}\} + \sin^{-1} (n_3/n_2)$ where $n_2$ and $n_3$ are the refractive indices of said core and cladding of said second fiber-optic block.

10. A detector according to claim 7, wherein said third fiber-optic block has a tapered shape for gradually reducing a sectional area of said third fiber-optic block perpendicular to the optical axis from said input end face to said output end face.

11. A detector according to claim 7, wherein said second fiber-optic block has an input-side effective numerical aperture which is not more than an output-side effective numerical aperture of said first fiber-optic block.

12. A detector according to claim 7, further comprising means for comparing an electrical fingerprint image output from said CCD with another fingerprint image.

13. A fiber optics block constituted by joining fiber optics blocks each formed to have two flat end faces by bundling optical fibers each having a core and a cladding, comprising:

a first fiber-optic block having an input surface inclined by a predetermined angle $\beta_0$ with respect to an optical axis thereat, the inclination angle $\beta_0$ being set to be smaller than a critical angle at which light coming from air on said core is reflected as total internal reflection at an interface between said core and said cladding of said first fiber-optic block; and a second fiber-optic block which is constituted by forming optical absorbers respectively between said optical fibers and has an input end face inclined by a predetermined angle $\beta_1$ with respect to an optical axis thereat and joined to said first fiber-optic block and an output end face perpendicular to an optical axis thereat, the predetermined angle $\beta_1$ being set to be smaller than a critical angle at which background light coming from air through said first fiber-optic block is reflected as total internal reflection at an interface between a core and cladding of said second fiber-optic block.

14. A block according to claim 13, wherein the inclination angle $\beta_0$ of said first fiber-optic block satisfies $\beta_0 < \sin^{-1}(n_1/n_0) - \sin^{-1}(n/n_0)$ where n, $n_1$, and $n_2$ are the refractive indices of air, said core, and said cladding of said first fiber-optic block, respectively.

15. A block according to claim 13, wherein the predetermined angle $\beta_1$ of said second fiber-optic block satisfies $\beta_1 < \sin^{-1}\{1/n_2(n_1^2 - ((n_0^2 - n^2)^{1/2} \sin\beta_0 + n_1 \cos\beta_0)^2)^{1/2}\} + \sin^{-1}(n_3/n_2)$ where $n_2$ and $n_3$ are the refractive indices of said core and cladding of said second fiber-optic block.

16. A block according to claim 13, wherein said second fiber-optic block has a tapered shape for gradually reducing a sectional area of said second fiber-optic block perpendicular to the optical axis from said input end face to said output end face.

17. A block according to claim 13, wherein said second fiber-optic block has an input-side effective numerical aperture which is not more than an output-side effective numerical aperture of said first fiber-optic block.

18. A fiber optics block constituted by joining fiber optics blocks each formed to have two flat end faces by bundling optical fibers each having a core and a cladding, comprising:

a first fiber-optic block having an input surface inclined by a predetermined angle $\beta_0$ with respect to an optical axis thereat, the inclination angle $\beta_0$ being set to be smaller than a critical angle at which light coming from air on said core is reflected as total internal reflection at an interface between said core and said cladding of said first-optic block;

a second fiber-optic block which is constituted by forming optical absorbers respectively between said optical fibers and has an input end face inclined by a predetermined angle $\beta_1$ with respect to an optical axis thereat and joined to said first fiber-optic block and an output end face perpendicular to an optical axis thereat, the predetermined angle $\beta_1$ being set to be smaller than a critical angle at which background light coming from air through said first fiber-optic block is reflected as total internal reflection at an interface between a core and cladding of said second fiber-optic block; and a third fiber-optic block having an input end face joined to said output end face of said second fiber-optic block to allow light incident from said second fiber-optic block to propagate and emerge from an output end face of said third fiber-optic block.

19. A block according to claim 18, wherein the inclination angle $\beta_0$ of said first fiber-optic block satisfies $\beta_0 < \sin^{-1}(n_1/n_0) - \sin^{-1}(n/n_0)$ where n, $n_1$, and $n_2$ are the refractive indices of air, said core, and said cladding of said first fiber-optic block, respectively.

20. A block according to claim 18, wherein the predetermined angle $\beta_1$ of said second fiber-optic block satisfies $\beta_1 < \sin^{-1}\{1/n_2(n_1^2 - ((n_0^2 - n^2)^{1/2} \sin\beta_0 + n_1 \cos\beta_0)^2)^{1/2}\} + \sin^{-1}(n_3/n_2)$ where $n_2$ and $n_3$ are the refractive indices of said core and cladding of said second fiber-optic block.

21. A block according to claim 18, wherein said third fiber-optic block has a tapered shape for gradually reducing a sectional area of said third fiber-optic block perpendicular to the optical axis from said input end face to said output end face.

22. A block according to claim 18, wherein said second fiber-optic block has an input-side effective numerical aperture which is not more than an output-side effective numerical aperture of said first fiber-optic block.

* * * * *